United States Patent
Sato et al.

(10) Patent No.: US 7,141,399 B2
(45) Date of Patent: Nov. 28, 2006

(54) PROCESS FOR THE PRODUCTION OF DIGLYCERIDES

(75) Inventors: Manabu Sato, Ibaraki (JP); Masami Shimizu, Ibaraki (JP); Jun Kohori, Ibaraki (JP); Minoru Kase, Ibaraki (JP); Takaaki Watanabe, Ibaraki (JP); Kazuhiro Onozuka, Ibaraki (JP)

(73) Assignee: Kao Corporation, Tokyo (JP)

( * ) Notice: Subject to any disclaimer, the term of this patent is extended or adjusted under 35 U.S.C. 154(b) by 146 days.

(21) Appl. No.: 10/499,819

(22) PCT Filed: Dec. 27, 2002

(86) PCT No.: PCT/JP02/13794

§ 371 (c)(1),
(2), (4) Date: Jul. 2, 2004

(87) PCT Pub. No.: WO03/060139

PCT Pub. Date: Jul. 24, 2003

(65) Prior Publication Data
US 2005/0214914 A1 Sep. 29, 2005

(30) Foreign Application Priority Data
Jan. 15, 2002 (JP) .............................. 2002-005649

(51) Int. Cl.
*C12P 7/64* (2006.01)
(52) U.S. Cl. .................................................... 435/134
(58) Field of Classification Search ...................... None
See application file for complete search history.

(56) References Cited

U.S. PATENT DOCUMENTS 5,219,744 A * 6/1993 Kurashige et al. .......... 435/135
6,716,610 B1 * 4/2004 Shimizu et al. ............. 435/134

FOREIGN PATENT DOCUMENTS

| EP | 307 154 | | 3/1989 |
| JP | 63-133992 | | 6/1988 |
| JP | 04071491 A | * | 3/1992 |
| JP | 05-041991 | | 2/1993 |
| JP | 10-234391 | | 9/1998 |

OTHER PUBLICATIONS

The term "Acid Value" on line dictionary at the web_http://www.the freedictionary.com, p. 1-2.*

* cited by examiner

*Primary Examiner*—Jean C. Witz
*Assistant Examiner*—Satyendra K. Singh
(74) *Attorney, Agent, or Firm*—Oblon, Spivak, McClelland, Maier & Neustadt, P.C.

(57) ABSTRACT

Provided is a preparation process of diglycerides which comprises reacting a fatty acid or lower alkyl ester thereof with glycerin in the presence of an immobilized partial glyceride lipase while removing water, which is generated upon reaction, out of the system. The reaction is preferably terminated when the acid value (AV) of the reaction mixture satisfies the following range: 50R-60>AV>70R-150 (with the proviso that AV>0). The present process makes it possible to efficiently prepare a high purity of diglycerides without impairing lipase activity even under reduced pressure. The present process is effective without being influenced by variations in reaction conditions such as fatty acid/glycerin ratio, reaction temperature or enzyme concentration. Particularly, even when the fatty acid/glycerin ratio is high, a high purity of diglycerides can be produced at a high reaction yield.

16 Claims, No Drawings

PROCESS FOR THE PRODUCTION OF DIGLYCERIDES

TECHNICAL FIELD

The present invention relates to a process for efficiently producing a high purity of diglycerides.

BACKGROUND ART

Diglycerides are used as an additive for improving plasticity of oils or fats or in the fields of foods, pharmaceuticals, cosmetics, etc. Foods utilizing the excellent physiological activity of diglycerides have recently drawn attentions.

As a typical production process of diglycerides, esterification or ester exchange reaction can be given. For example, a process of obtaining diglycerides by reacting a fatty acid or a lower alkyl ester thereof with glycerin in the presence of immobilized 1,3-specific lipase and taking the resulting water or lower alcohol, which is generated upon the reaction, out of the system by pressure reduction is known (Japanese Patent Publication No. Hei 6-65311).

Since not only diglycerides but also triglycerides are prepared by the esterification reaction using 1,3-specific lipase, a rise in the reaction yield decreases the purity of diglycerides. Decreasing in the reaction yield, on the other hand, increases the purity of diglycerides, but a large amount of glycerin or fatty acid remains unreacted. In order to increase the purity of diglycerides, a purification step such as stripping is therefore inevitable after esterification reaction.

As a method for overcoming the above-described problem, proposed is a process for preparing triglyceride-free glycerides by using partial glyceride lipase which does not act on triglycerides (Japanese Patent Application Laid-Open No. Sho 61-181390). This method is however not suited for the production of a high purity of diglycerides, because monoglycerides are main products of this method.

In the conventional esterification reaction which has been employed industrially, it is necessary to remove, out of the system, water generated with the progress of the reaction, and shift the reaction equilibrium, thereby increasing the reaction yield. The esterification reaction using a partial glyceride lipase while removing water out of the system under reduced pressure involves problems such as termination of the esterification reaction before termination. Also proposed is a process (Japanese Patent Application Laid-Open No. Hei 1-137989), in the synthesis of triglycerides by acting a partial glyceride lipase on an oil or fat containing partial glycerides and fatty acids, of carrying out the esterification reaction under a low water content while using an immobilized enzyme. This process is for the synthesis of triglycerides while suppressing the yields of mono- and diglycerides, and is essentially different from the process for preparing a high purity of diglycerides.

When diglycerides are synthesized by the esterification reaction, the optimum terminal point of the reaction for attaining a high diglyceride purity at a high reaction yield, depending on the substrate ratio, as raw materials, of a fatty acid or ester thereof to glycerin, reaction temperature, enzyme concentration or the like. Particularly when a ratio of the fatty acid or ester thereof to glycerin is raised for improving a reaction rate, an increase in a reaction yield by prolonging the reaction leads to a problem such as decreasing in a diglycerides purity due to the formation of triglycerides.

DISCLOSURE OF THE INVENTION

An object of the present invention is therefore to provide a process for efficiently producing a high purity of diglycerides without impairing lipase activity even under reduced pressure.

Another object of the present invention is to provide a process for producing a high purity of diglycerides at a high reaction yield, without being influenced by variations of a fatty acid/glycerin ratio, reaction temperature or enzyme concentration, particularly when the fatty acid/glycerin ratio is set high.

The present inventor has found that by reacting a fatty acid or lower alkyl ester thereof with glycerin in the presence of an immobilized partial glyceride lipase, while removing water, which is generated upon reaction, out of the reaction system, a diglycerides formation ratio shows a drastic increase and a high purity of diglycerides can be obtained with high yield, compared with the reaction in the presence of an un-immobilized partial glyceride lipase. The present inventor has also found that termination of the reaction when the acid value of the reaction mixture falls within a predetermined range in relation to a feed ratio of a fatty acid or lower alkyl ester thereof to glycerin makes it possible to produce a high purity of diglycerides at a reaction yield as high as possible.

In one aspect of the present invention, there is thus provided a process for preparing diglycerides, which comprises reacting a fatty acid or lower alkyl ester thereof with glycerin in the presence of an immobilized partial glyceride lipase, while removing water, which is generated upon reaction, out of the system.

In another aspect of the present invention, there is also provided a process for producing diglycerides as described above, wherein the reaction is terminated when the acid value (AV) of the reaction mixture falls within a range satisfying $50R-55>AV>70R-150$ (with the proviso that $AV>0$).

BEST MODE FOR CARRYING OUT THE INVENTION

The partial glyceride lipase to be used in the present invention is a lipase which hydrolyzes partial glycerides such as monoglycerides and diglycerides but does not hydrolyze triglycerides. Examples of the partial glyceride lipase include monoglyceride lipase or diglyceride lipase derived from animal organs such as rat small intestine or pig fat tissue, monoglyceride lipase derived from Bacillus sp. H-257 (J. Biochem., 127, 419–425, 2000), monoglyceride lipase derived from *Pseudomonas* sp. LP7315 (Journal of Bioscience and Bioengineering, 91(1), 27–32, 2001), lipase derived from *Penicillium cyclopium* (J. Biochem, 87(1), 205–211, 1980), and lipase derived from *Penicillium camembertii* U-150 (J. Fermentation and Bioengineering, 72(3), 162–167, 1991). Examples of its commercially available product include "Monoglyceride Lipase (MGLPII)" (product of Asahi Kasei Corp.) and "Lipase G Amano 50" (product of Amano Enzyme Inc.). Particularly when a polyunsaturated fatty acid (meaning an unsaturated fatty acid having at least four double bonds) or lower alkyl ester thereof is used as a reaction substrate, a partial glyceride lipase having an optimal temperature within a range of 30° C. or greater but less than 50° C. is preferably employed.

The immobilized partial glyceride lipase to be used in the present invention has the above-described partial glyceride lipase immobilized to a carrier. Examples of the immobilizing carrier include inorganic carriers such as CELITE, diatomaceous earth, kaolinite, silica gel, molecular sieves, porous glass, activated charcoal, calcium carbonate and ceramics; and organic polymers such as cellulose powder, polyvinyl alcohol, polypropylene, chitosan, ion exchange resin, hydrophobic adsorption resin, chelate resin or synthetic adsorption resin. Partial glyceride lipase immobilized to an ion exchange resin is particularly preferred from the viewpoint of water retention power.

As the ion exchange resin, a porous anion exchange resin is preferred. The particle size of the resin is preferably 100 to 1000 µm, while the pore size is desirably 100 to 1500 Å. When the resin is in the form of pores, the surface area for enzyme adsorption becomes large, bringing about an increase in the adsorption amount. As the material of the resin, phenol-formaldehyde, polystyrene, acrylamide and divinylbenzene are usable. Particularly desired is phenol-formaldehyde resin (trade name; "Duolite A-568").

No limitation is imposed on the immobilization temperature of the partial glyceride lipase insofar as it does not deactivate the enzyme, and it may be 0 to 60° C., with 5 to 30° C. being particularly preferred. The pH of an aqueous enzyme solution used for immobilization may fall within a range not causing modification of the enzyme, preferably from 3 to 9. Particularly when lipase whose optimum pH is acidic is employed, the pH is preferably adjusted to 4 to 6 in order to attain the maximum activity. As a buffer used for the preparation of the aqueous enzyme solution, ordinarily employed ones such as acetate buffer, phosphate buffer and Tris-HCL buffer are usable. The concentration of the partial glyceride lipase in the aqueous enzyme solution is preferably lower than the solubility of the enzyme but is sufficient from the viewpoint of the immobilizing efficiency. The supernatant after removal of the insoluble portion by centrifugal separation may be used if desired. The partial glyceride lipase is preferably used in an amount of from 0.05 to 10 parts by weight, particularly from 0.1 to 5 parts by weight, relative to 1 part by weight of the immobilizing carrier.

In the present invention, the immobilizing carrier is preferably treated with one or more lipophilic fatty acids or derivatives thereof prior to immobilization in order to impart it with an adsorption state permitting exhibition of high activity. They may be used singly, but use of two or more of them in combination is more effective. As a contact method of these lipophilic fatty acids or derivatives thereof with an immobilizing carrier, they may be added as are to water or an organic solvent, or alternatively, in order to improve their dispersibility, the lipophilic fatty acids or derivatives thereof may be dispersed or dissolved in an organic solvent in advance, followed by the addition to the immobilizing carrier dispersed in water. Examples of the organic solvent include chloroform, hexane and ethanol. The lipophilic fatty acid or derivative thereof may be added in an amount of from 0.01 to 1 part by weight (dry weight), particularly preferably from 0.05 to 0.5 part by weight, relative to 1 part of the immobilizing carrier. The contact temperature may range from 0 to 100° C., with 20 to 60° C. being particularly preferred. The contact time may be from 5 minutes to 5 hours. The immobilizing carrier is collected by filtration after the above-described treatment. It may be dried upon collection. The drying temperature may preferably range from room temperature to 100° C. Drying can also be carried out under reduced pressure.

Examples of the lipophilic fatty acid used for treatment of the immobilizing carrier include linear or branched, saturated or unsaturated fatty acids which have 4 to 24 carbon atoms and may be substituted with a hydroxyl group. Preferred examples include $C_{8-18}$ fatty acids including linear saturated fatty acids such as capric acid, lauric acid and myristic acid, unsaturated fatty acids such as oleic acid and linoleic acid, hydroxyfatty acids such as ricinolic acid, and branched fatty acids such as isostearic acid. Examples of the derivatives of a lipophilic fatty acid include esters between a $C_{8-18}$ fatty acid and a hydroxyl-containing compound, such as monohydric alcohol esters, polyhydric alcohol esters, phospholipids and derivatives obtained by adding ethylene oxide to the exemplified ester. Examples of the monohydric alcohol ester include methyl esters and ethyl esters, while those of the polyhydric alcohol ester include monoglycerides, diglycerides, derivatives of these glycerides, polyglycerin fatty acid esters, sorbitan fatty acid esters, and sucrose fatty acid esters. It is preferred from the viewpoint of facilitating this treatment step that these fatty acids or derivatives thereof preferably take the liquid form at normal temperature. As these fatty acids or derivatives thereof, mixtures of the above-described fatty acids, for example, naturally occurring fatty acids such as soybean fatty acid are usable.

As the fatty acid to be used in the reaction of the present invention between the fatty acid or lower alkyl ester thereof and glycerin in the presence of the immobilized partial glyceride lipase, saturated or unsaturated $C_{4-22}$ fatty acids are preferred. Examples include butyric acid, valeric acid, caproic acid, enantoic acid, caprylic acid, pelargonic acid, capric acid, undecanoic acid, lauric acid, myristic acid, palmitic acid, zoomaric acid, stearic acid, oleic acid, elaidic acid, linoleic acid, linolenic acid, arachidonic acid, behenic acid, erucic acid, eicosapentaenoic acid and docosahexaenoic acid. As the lower alcohol which will form an ester with the above-described fatty acid, lower alcohols having 1 to 3 carbon atoms are preferred. Examples of the $C_{1-3}$ lower alcohol include methanol, ethanol, 1-propanol and 2-propanol. The above-described fatty acids or lower alkyl esters thereof may be used in combination. A mixture of the fatty acids, for example, naturally occurring fatty acid such as soybean fatty acid is also usable.

In the above-described reaction, the fatty acid or ester thereof and glycerin are reacted preferably at a molar ratio R [R=fatty acid or lower alkyl ester thereof (mol)/glycerin (mol)] of 1.5 to 2.6, more preferably 1.6 to 2.5, especially 1.8 to 2.3.

The reaction between the fatty acid or ester thereof and glycerin is effected in the presence of the immobilized partial glyceride lipase while removing water, which is generated by the reaction, out of the system. More specifically, the reaction is conducted under substantially water-free conditions except water contained in the lipase preparation, and water generated upon the esterification reaction is taken out of the system by the method such as reduction in pressure, use of an absorbent such as zeolite or molecular sieves, or introduction of a dried inert gas into the reaction tank.

The temperature of the esterification reaction varies, depending on the melting point of the raw materials or the product, or heat stability of the enzyme employed, but is preferably 20 to 80° C., especially 30 to 70° C. from the viewpoint of reactivity. Particularly when a polyunsaturated fatty acid or alkyl ester thereof is used as a reaction substrate, the reaction temperature is preferably set at 30° C. or greater but less than 50° C. The reaction time is preferably within 10 hours from the viewpoint of industrial productivity.

The process of the present invention makes it possible to produce diglycerides having a diglyceride purity [diglycerides/(diglycerides+triglycerides)×100] of 80 wt. % or greater, more preferably 85 wt. % or greater, especially 90 wt. % or greater at a reaction yield (percentage of the total weight of diglycerides and triglycerides in the reaction mixture) as high as 60 wt. % or greater, preferably 65 wt. % or greater, more preferably 70 wt. % or greater.

In order to increase the diglyceride purity of the diglycerides thus obtained, the reaction is effected while measuring the acid value (AV) of the reaction mixture at appropriate time intervals. It is preferred to terminate the reaction when, the acid value falls within the following range: 50R-55>AV>70R-150 (with the proviso that AV>0) in order to attain the reaction yield of 60 wt. % or greater and diglyceride purity of 80 wt. % or greater. It is more preferred to terminate the reaction at the acid value falling within the following range: 50R-70>AV>70R-145 (with the proviso that AV>0) in order to attain the reaction yield of 70 wt. % or greater and diglyceride purity of 85 wt. % or greater, and particularly, at the acid value falling the following range: 50R-80>AV>70R-140 (with the proviso that AV>0) in order to attain the reaction yield of 80 wt. % or greater and diglyceride purity of 90 wt. % or greater.

When the reaction is conducted under the conditions as described above, it is possible to produce a high purity of diglycerides at a reaction yield as high as possible without being influenced by variations, if any, in the reaction condition such as a raw material substrate ratio, reaction temperature or enzyme concentration. When the reaction is terminated at an acid value higher than the above-described range, high productivity cannot be attained because of a low reaction yield in spite of a high diglyceride purity. When the reaction is terminated at an acid value lower than the above-described range, on the other hand, a ratio of triglycerides in the reaction mixture increases, making it impossible to attain a sufficient diglyceride purity. Termination of the reaction at an acid value outside the above-described range is therefore not preferred.

EXAMPLE

Example 1

In a 0.1 mol/L aqueous solution of sodium hydroxide, 10 g of "Duolite A-568" (product of Rohm & Haas, average particle size: 480 µm) was stirred for 1 hour. After stirring, the equilibrium of the pH of the reaction mixture was established for 2 hours with 100 mL of a 500 mM acetate buffer (pH 5). The equilibrium of pH was then established for two hours twice with 100 mL of a 50 mM acetate buffer (pH 5). The mixture was filtered to collect the carrier, followed by ethanol substitution with 50 mL of ethanol for 30 minutes. After filtration, 50 mL of ethanol containing 10 g of ricinolic acid was added to cause the ricinolic acid to adsorb to the carrier for 30 minutes. After collection by filtration, the carrier was washed four times with 50 mL of a 50 mM acetate buffer (pH 5). Ethanol was then removed and the residue was filtered to collect the carrier. Then, an enzyme solution having 20 g of commercially available partial glyceride lipase (Lipase G "Amano" 50, product of Amano Enzyme Inc.) dissolved in 180 mL of a 50 mM acetate buffer (pH 5) was brought into contact with the carrier for 2 hours to immobilize the lipase on it. The immobilized enzyme was collected by filtration and washed with 50 mL of a 50 mM acetate buffer (pH 5) to remove the enzyme or protein which had not been immobilized. The above-described operations were each carried out at 20° C. An immobilization ratio was determined from a difference between the residual activity of the enzyme solution after immobilization and activity of the enzyme solution before immobilization, resulting in 95%. Soybean fatty acid (40 g) serving as a substrate for the actual reaction was added, followed by dehydration at 40° C. under reduced pressure. The residue was then filtered to separate from the soybean fatty acid, whereby an immobilized enzyme was obtained.

The immobilized enzyme (20 g, dry weight: 8 g) thus obtained was weighed in a 200 mL four-necked flask. Soybean fatty acid and glycerin (80 g in total, at a molar ratio of fatty acid/glycerin=2.0) were added, followed by esterification reaction for 7 hours at 40° C. under reduced pressure, while measuring the acid value of the reaction mixture at appropriate time intervals. The acid value of the reaction mixture at that time was 9.6. After trimethylsilylation, the reaction mixture was subjected to gas chromatography to analyze a glyceride composition and unreacted substances. The results are shown in Table 1. It was found that the reaction yield was 90.4% and diacylglycerol (DG) purity was as high as 96.7%.

Example 2

In a similar manner to Example 1, an immobilized enzyme was prepared using, as a carrier, "Duolite A-568" crashed to have an average particle size of 320 µm.

In a 200 mL four-necked flask, 10 g (dry weight: 4 g) of the immobilized enzyme thus obtained was weighed. Soybean fatty acid and glycerin (80 g in total, at a molar ratio of fatty acid/glycerin=2.0) were added, followed by esterification reaction for 7 hours at 50° C. under reduced pressure while measuring the acid value of the reaction mixture at appropriate time intervals. The acid value of the reaction mixture at that time was 8.6. The reaction mixture was analyzed in a similar manner to Example 1, resulting in a reaction yield of 89.1% and a DG purity as high as 96.9%.

Example 3

In a 200 mL four-necked flask, 10 g (dry weight: 4 g) of the immobilized enzyme obtained in Example 1 was weighed. Soybean fatty acid and glycerin (80 g in total, at a molar ratio of fatty acid/glycerin=2.0) were added, followed by esterification reaction for 3 hours at 50° C. under reduced pressure while measuring the acid value of the reaction mixture at appropriate time intervals. The acid value of the reaction mixture at that time was 33.4. The reaction mixture was analyzed in a similar manner to Example 1, resulting in a reaction yield of 71.0% and a DG purity as high as 99.1%.

Example 4

In a 200 mL four-necked flask, 10 g (dry weight: 4 g) of the immobilized enzyme obtained in Example 1 was weighed. Soybean fatty acid and glycerin (80 g in total, at a molar ratio of fatty acid/glycerin=2.0) were added, followed by esterification reaction for 2.6 hours at 50° C. under reduced pressure while measuring the acid value of the reaction mixture at appropriate time intervals. The acid value of the reaction mixture at that time was 44.4. The reaction mixture was analyzed in a similar manner to Example 1, resulting in a reaction yield of 65.6% and a DG purity as high as 99.2%.

Example 5

In a 200 mL four-necked flask, 20 g (dry weight: 8 g) of the immobilized enzyme obtained in Example 1 was weighed. Soybean fatty acid and glycerin (80 g in total, at a molar ratio of fatty acid/glycerin=1.83) were added, followed by esterification reaction for 8 hours at 40° C. under reduced pressure while measuring the acid value of the reaction mixture at appropriate time intervals. The acid value of the reaction mixture at that time was 5.2. The reaction mixture was analyzed in a similar manner to Example 1, resulting in a reaction yield of 82.9% and a DG purity as high as 92.9%.

Example 6

In a 200 mL four-necked flask, 20 g (dry weight: 8 g) of the immobilized enzyme obtained in Example 1 was weighed. Soybean fatty acid and glycerin (80 g in total, at a molar ratio of fatty acid/glycerin=2.25) were added, followed by esterification reaction for 4 hours at 40° C. under reduced pressure while measuring the acid value of the reaction mixture at appropriate time intervals. The acid value of the reaction mixture at that time was 22.6. The reaction mixture was analyzed in a similar manner to Example 1, resulting in a reaction yield of 84.0% and a DG purity as high as 90.5%.

Example 7

In a 200 mL four-necked flask, 20 g (dry weight: 8 g) of the immobilized enzyme obtained in Example 1 was weighed. Soybean fatty acid and glycerin (80 g in total, at a molar ratio of fatty acid/glycerin=2.47) were added, followed by esterification reaction for 3.3 hours at 40° C. under reduced pressure while measuring the acid value of the reaction mixture at appropriate time intervals. The acid value of the reaction mixture at that time was 33.2. The reaction mixture was analyzed in a similar manner to Example 1, resulting in a reaction yield of 80.2% and a DG purity as high as 90.0%.

Comparative Example 1

In a 200 mL four-necked flask, 4 g of "Lipozyme RMIM" (product of Novozymes), which was 1,3-specific lipase, was weighed. Soybean fatty acid and glycerin (80 g in total, at a molar ratio of fatty acid/glycerin=2.0) were added, followed by esterification reaction for 7 hours at 50° C. under reduced pressure while measuring the acid value of the reaction mixture at appropriate time intervals. The acid value of the reaction mixture at that time was 2.6. The reaction mixture was analyzed in a similar manner, resulting in a reaction yield of 90.8% and a DG purity as low as 72.6%.

Comparative Example 2

In a 200 mL four-necked flask, 2 g of a commercially available partial glyceride lipase (Lipase G "AMANO" 50, product of Amano Enzyme Inc.) which had not been immobilized was weighed. Soybean fatty acid and glycerin (80 g in total, at a molar ratio of fatty acid/glycerin=2.0) were added, followed by esterification reaction for 7 hours at 40° C. under reduced pressure while measuring the acid value of the reaction mixture at appropriate time intervals. The acid value of the reaction mixture at that time was 140.4. The reaction mixture was analyzed in a similar manner, resulting in a reaction yield of 14.6%. The reaction did not proceed and an excessive amount of unreacted substances remained.

Comparative Example 3

In a 200 mL four-necked flask, 10 g (dry weight: 4 g) of the immobilized enzyme obtained in Example 1 was weighed. Soybean fatty acid and glycerin (80 g in total, at a molar ratio of fatty acid/glycerin=2.0) were added, followed by esterification reaction for 2.2 hours at 50° C. under reduced pressure while measuring the acid value of the reaction mixture at appropriate time intervals. The acid value of the reaction mixture at that time was 57.0. The reaction mixture was analyzed in a similar manner to Example 1, resulting in a DG purity as high as 99.3% but a reaction yield as low as 59.8%.

Comparative Example 4

In a 200 mL four-necked flask, 20 g (dry weight: 8 g) of the immobilized enzyme obtained in Example 1 was weighed. Soybean fatty acid and glycerin (80 g in total, at a molar ratio of fatty acid/glycerin=2.25) were added, followed by esterification reaction for 11 hours at 40° C. under reduced pressure while measuring the acid value of the reaction mixture at appropriate time intervals. The acid value of the reaction mixture at that time was 7.0. The reaction mixture was analyzed in a similar manner to Example 1, resulting in a reaction yield of 94.4% and a DG purity as low as 71.4%.

Comparative Example 5

In a 200 mL four-necked flask, 20 g (dry weight: 8 g) of the immobilized enzyme obtained in Example 1 was weighed. Soybean fatty acid and glycerin (80 g in total, at a molar ratio of fatty acid/glycerin=2.47) were added, followed by esterification reaction for 8 hours at 40° C. under reduced pressure while measuring the acid value of the reaction mixture at appropriate time intervals. The acid value of the reaction mixture at that time was 18.0. The analysis of the reaction mixture was made in a similar manner to Example 1, resulting in a reaction yield of 89.8%, but a DG purity as low as 66.3%.

TABLE 1

| | Composition of reaction mixture (%) | | | | | Substrate molar ratio FA/Gly | Reaction yield (%) DG + TG | Acid value upon completion of reaction | DG purity (%) DG/(DG + TG) × 100 |
|---|---|---|---|---|---|---|---|---|---|
| | Unreacted FA | Unreacted Gly | MG | DG | TG | | | | |
| Ex. 1 | 4.8 | 0.0 | 4.7 | 87.5 | 2.9 | 2.0 | 90.4 | 9.6 | 96.7 |
| Ex. 2 | 4.3 | 0.0 | 6.7 | 86.3 | 2.8 | 2.0 | 89.1 | 8.6 | 96.9 |
| Ex. 3 | 16.7 | 0.1 | 12.2 | 70.4 | 0.6 | 2.0 | 71.0 | 33.4 | 99.1 |
| Ex. 4 | 22.2 | 0.3 | 11.9 | 65.1 | 0.5 | 2.0 | 65.6 | 44.4 | 99.2 |

TABLE 1-continued

|  | Composition of reaction mixture (%) | | | | | Substrate molar ratio FA/Gly | Reaction yield (%) DG + TG | Acid value upon completion of reaction | DG purity (%) DG/(DG + TG) × 100 |
|---|---|---|---|---|---|---|---|---|---|
|  | Unreacted FA | Unreacted Gly | MG | DG | TG | | | | |
| Ex. 5 | 2.6 | 0.3 | 14.2 | 77.0 | 5.9 | 1.83 | 82.9 | 5.2 | 92.9 |
| Ex. 6 | 11.3 | 0.0 | 4.7 | 76.0 | 8.0 | 2.25 | 84.0 | 22.6 | 90.5 |
| Ex. 7 | 16.6 | 0.0 | 3.2 | 72.2 | 8.0 | 2.47 | 80.2 | 33.2 | 90.0 |
| Comp. Ex. 1 | 1.3 | 0.1 | 7.8 | 65.9 | 24.9 | 2.0 | 90.8 | 2.6 | 72.6 |
| Comp. Ex. 2 | 70.2 | 1.8 | 13.4 | 14.2 | 0.4 | 2.0 | 14.6 | 140.4 | 97.3 |
| Comp. Ex. 3 | 28.5 | 0.4 | 11.3 | 59.3 | 0.5 | 2.0 | 59.8 | 57.0 | 99.3 |
| Comp. Ex. 4 | 3.5 | 0.0 | 2.1 | 67.4 | 27.0 | 2.25 | 94.4 | 7.0 | 71.4 |
| Comp. Ex. 5 | 9.0 | 0.0 | 1.2 | 59.5 | 30.3 | 2.47 | 89.8 | 18.0 | 66.3 |

FA: fatty acid
Gly: glycerin
MG: monoglycerides
DG: diglycerides
TG: triglycerides The preparation processes (Examples 1 to 7) of the present invention made it possible to prepare diglycerides having a diglyceride purity of 90% or greater at a markedly high reaction yield.

Example 8

The immobilized enzyme obtained in Example 1 was washed with a polyunsaturated-fatty-acid-containing fatty acid (DHA content: 44 wt. %), which acid is a substrate in the actual reaction. In a 200 mL four-necked flask, 20 g (dry weight: 8 g) of the resulting immobilized enzyme was weighed. A polyunsaturated-fatty-acid-containing fatty acid (DHA content: 44%) and glycerin (80 g in total, at a molar ratio of fatty acid/glycerin=2.30) were added, followed by esterification reaction for 45 hours at 40° C. under reduced pressure, while measuring the acid value of the reaction mixture at appropriate time intervals. The acid value of the reaction mixture at that time was 27.8. The reaction mixture was then subjected to HPLC to analyze a glyceride composition and unreacted substances. In addition, a TLC plate spotted with the reaction mixture was developed (a developing solvent: chloroform/acetone/methanol=93.5/4.5/2.0 vol %) to separate it into each glyceride. After elution with ethyl acetate and desolventation, a fatty acid composition was analyzed by GC. The results are shown in Table 2. It was found that the reaction yield was 74.2% and the diglyceride (DG) purity was as high as 85.3%, while DHA content in the diglyceride was as high as 44%.

Example 9

The immobilized enzyme (20 g, dry weight: 8 g) obtained in Example 1 was, after washing, weighed in a 200 mL four-necked flask. A polyunsaturated-fatty-acid-containing fatty acid (DHA content: 44%) and glycerin (80 g in total, at a molar ratio of fatty acid/glycerin=1.87) were added, followed by esterification reaction for 165 hours at 40° C. under reduced pressure, while measuring the acid value of the reaction mixture at appropriate time intervals. The acid value of the reaction mixture at that time was 3.6. The reaction mixture was analyzed in a similar manner to Example 8, resulting in a reaction yield of 83.8% and the DG purity as high as 88.3%, while DHA content in DG was as high as 37%.

Comparative Example 6

In a 200 mL four-necked flask, 4 g of 1,3-specific lipase "Lipozyme RMIM" (product of Novozymes) was weighed as a commercially available immobilized enzyme. A polyunsaturated-fatty-acid-containing fatty acid (DHA content: 44%) and glycerin (80 g in total, at a molar ratio of fatty acid/glycerin=2.36) were added, followed by esterification reaction for 48 hours at 50° C. under reduced pressure, while measuring the acid value of the reaction mixture at appropriate time intervals. The acid value of the reaction mixture at that time was 45.2. The reaction mixture was analyzed in a similar manner to Example 8, resulting in a reaction yield of 57.1% and a DG purity, as low as 65.8%.

Comparative Example 7

The immobilized enzyme (20 g, dry weight: 8 g) obtained in Example 1 was, after washing, weighed in a 200 mL four-necked flask. A polyunsaturated-fatty-acid-containing fatty acid (DHA content: 44%) and glycerin (80 g in total, at a molar ratio of fatty acid/glycerin=2.66) were added, followed by esterification reaction for 18 hours at 40° C. under reduced pressure, while measuring the acid value of the reaction mixture at appropriate time intervals. The acid value of the reaction mixture at that time was 30.6. The reaction mixture was analyzed in a similar manner to Example 8, resulting in a reaction yield of 77.2% and a DG purity, as low as 66.2%.

TABLE 2

| | Composition of reaction mixture (%) | | | | | Substrate molar ratio FA/Gly | Reaction yield (%) DG + TG | Acid value upon completion of reaction | DG purity (%) DG/(DG + TG) × 100 | DHA content in DG (%) |
|---|---|---|---|---|---|---|---|---|---|---|
| | Unreacted FA | Unreacted Gly | MG | DG | TG | | | | | |
| Ex. 8 | 15.3 | 0.0 | 10.5 | 63.3 | 10.9 | 2.30 | 74.2 | 27.8 | 85.3 | 44 |
| Ex. 9 | 2.0 | 0.2 | 14.0 | 74.0 | 9.8 | 1.87 | 83.8 | 3.6 | 88.3 | 37 |
| Comp. Ex. 6 | 24.8 | 0.0 | 18.1 | 37.6 | 19.5 | 2.36 | 57.1 | 45.2 | 65.8 | 33 |
| Comp. Ex. 7 | 16.8 | 0.0 | 6.0 | 51.1 | 26.1 | 2.66 | 77.2 | 30.6 | 66.2 | 29 |

The invention claimed is:

1. A process for preparing diglycerides, which comprises reacting a fatty acid or lower alkyl ester thereof with glycerin in the presence of an immobilized partial glyceride lipase while removing water, which is generated upon reaction, out of the reaction system.

2. A process of claim 1, wherein the fatty acid or lower alkyl ester thereof and glycerin are reacted at a molar ratio R ranging from 1.5 to 2.6 wherein R=fatty acid or lower alkyl ester thereof (mol)/glycerin (mol).

3. A process of claim 1 or 2, wherein the immobilized partial glyceride lipase is obtained by immobilizing a partial glyceride lipase to an immobilizing carrier pretreated with a lipophilic fatty acid or derivative thereof.

4. A process of any one of claims 1 to 2, wherein diglycerides having a diglyceride concentration [diglycerides/(diglycerides+triglycerides)×100] of 80 wt. % or greater are obtained at a reaction efficiency (a total weight percentage of the diglycerides and triglycerides in the reaction mixture) of 60 wt. % or greater.

5. A process of any one of claims 1 to 2, wherein the reaction is terminated at an acid value (AV) of the reaction mixture satisfying the following range: ((50×R)−55)>AV>((70×R)−150) wherein R=fatty acid or lower alkyl ester thereof (mol)/glycerin (mol), (with the proviso that AV>0).

6. The process of claim 1, wherein said immobilized partial glyceride lipase is immobilized on at least one carrier selected from the group consisting of diatomaceous earth, kaolinite, silica gel, molecular sieves, porous glass, activated charcoal, calcium carbonate, ceramics, cellulose powder, polyvinyl alcohol, polypropylene, chitosan, ion exchange resin, hydrophobic adsorption resin, chelate resin and synthetic adsorption resin.

7. The process of claim 1, wherein said immobilized partial glyceride lipase is immobilized on an ion exchange resin.

8. The process of claim 7, wherein said ion exchange resin is a porous anion exchange resin having a particle size of 100–100 μm and a pore size of 100 to 1500 Å.

9. The process of claim 1, wherein said partial glyceride lipase is used in an amount of 0.05 to 10 part by weight relative to 1 part by weight of an immobilizing carrier.

10. The process of claim 6, wherein said carrier is treated with one or more lipophilic fatty acids or derivatives thereof prior to immobilization.

11. The process of claim 1, wherein said fatty acid or lower alkyl ester thereof is a saturated or unsaturated $C_{4-22}$ fatty acid.

12. The process of claim 1, wherein said fatty acid or lower alkyl ester thereof is at least one selected from the group consisting of butyric acid, valeric acid, caproic acid, enantoic acid, caprylic acid, pelargonic acid, capric acid, undecanoic acid, lauric acid, myristic acid, palmitic acid, zoomaric acid, stearic acid, oleic acid, elaidic acid, linoleic acid, linolenic acid, arachidonic acid, behenic acid, erucic acid, eicosapentaenoic acid and docosahexaenoic acid.

13. The process of claim 1 wherein said fatty acid or lower alkyl ester thereof is at least one lower alkyl ester of a lower alcohol selected from the group consisting of methanol, ethanol, 1-propanol and 2-propanol.

14. The process of claim 1, wherein said process has a diglyceride purity of 80 wt. % or greater at a reaction yield of 60 wt. % or greater.

15. The process of claim 1, wherein said process has a diglyceride purity of 85 wt. % or greater at a reaction yield of 60 wt. % or greater.

16. The process of claim 1, wherein said process has a diglyceride purity of 90 wt. % or greater at a reaction yield of 60 wt. % or greater.

* * * * *